United States Patent
McEntee

(10) Patent No.: US 6,648,853 B1
(45) Date of Patent: Nov. 18, 2003

(54) SEPTUM

(75) Inventor: John F. McEntee, Boulder Creek, CA (US)

(73) Assignee: Agilent Technologies Inc., Palo Alto, CA (US)

(*) Notice: Subject to any disclaimer, the term of this patent is extended or adjusted under 35 U.S.C. 154(b) by 69 days.

(21) Appl. No.: 09/703,304

(22) Filed: Oct. 31, 2000

(51) Int. Cl.[7] .............. B32B 3/10; B32B 3/28; B32B 3/30; B32B 27/08; A61M 37/00; A61M 5/14; A61M 31/00; B01L 3/02; B01L 3/00

(52) U.S. Cl. .................. 604/88; 428/131; 428/167.02; 428/577; 604/86; 604/256; 604/288.02; 422/100; 422/102

(58) Field of Search .............. 428/131; 604/167.02, 604/86, 88, 256, 288.02; 600/577; 422/100, 102

(56) References Cited

U.S. PATENT DOCUMENTS

| | | | |
|---|---|---|---|
| 4,190,040 A | 2/1980 | Schulte | |
| 4,543,088 A * | 9/1985 | Bootman et al. | 604/93 |
| 4,710,167 A | 12/1987 | Lazorthes | |
| 4,857,053 A * | 8/1989 | Dalton | 604/93 |
| 5,482,591 A * | 1/1996 | Reo | 156/306.6 |
| 5,575,769 A * | 11/1996 | Vaillancourt | 604/86 |
| 5,639,810 A * | 6/1997 | Smith, III et al. | 524/269 |
| 6,149,632 A * | 11/2000 | Landuyt | 604/256 |
| 6,165,138 A * | 12/2000 | Miller | 600/577 |
| 6,361,744 B1 * | 3/2002 | Levy | 422/99 |

FOREIGN PATENT DOCUMENTS

EP    0 546 220    2/1996

* cited by examiner

Primary Examiner—Harold Pyon
Assistant Examiner—Patricia L. Nordmeyer
(74) Attorney, Agent, or Firm—Gordon M. Stewart

(57) ABSTRACT

A septum penetrable by a member and which maintains a seal following member penetration in an axial direction and withdrawal. The septum includes a first layer of resilient material having first and second opposed surfaces, and a second layer extending across the first surface of the first layer and which is in radial tension. A third layer under tension may extend across the second surface. Septum assemblies and methods of fabricating the septa are also provided.

13 Claims, 4 Drawing Sheets

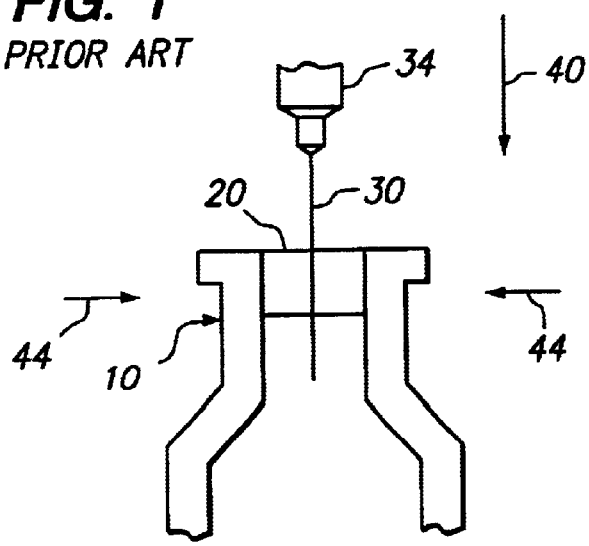
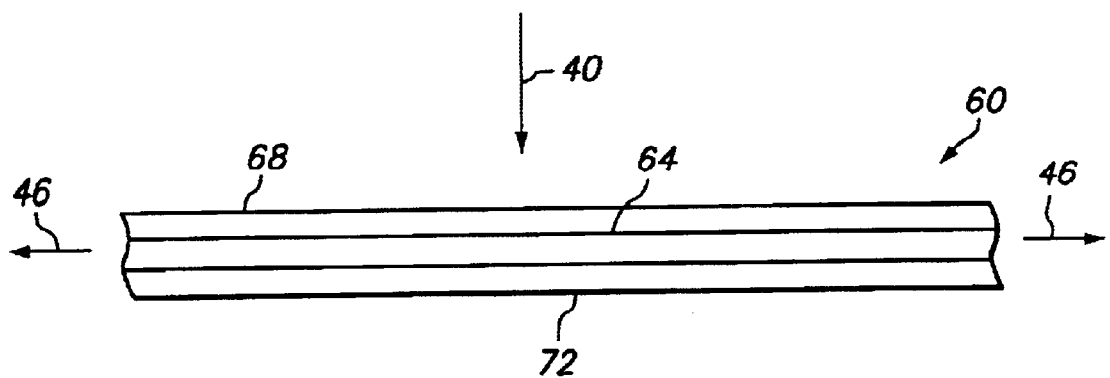

SEPTUM

FIELD OF THE INVENTION

This invention relates to septa which are widely used in the chemical, medical, and biochemical industries.

BACKGROUND OF THE INVENTION

Septa are piercable, mechanical barriers typically positioned between a vessel and its contents (usually a liquid) and the vessel's ambient environment. In such a configuration a septum prevents contamination of the vessel contents or contamination of the environment by the vessel contents. A conventional septum 20 is illustrated in FIG. 1. Access to a vessel 10 is gained by piercing septum 20 in an axial direction 40 with a small gauge tubing such as a hypodermic needle 30 on a syringe 34, which may then used to transfer liquid or other material into or out of vessel 20. A typical septum 20 is comprised of rubber or other elastomeric material, pressed or otherwise inserted into a rigid collar, such as a vessel neck or cap so as to hold the elastomer under radial compression (direction 44 in FIG. 1). When pierced by a small gauge tube, the compressed elastomer creates a seal around the tube with a radial reaction force. When the tube is withdrawn, the compressed elastomer forces the hole closed, thus, resealing the vessel.

To function as described above, the septum must be able to contain compressive forces in the axial direction during tubing penetration and withdrawal. This is conventionally done by making the dimension of the septum in the axial direction (the septum "thickness") deep enough to resist the compressive forces at the septum center. To improve the sealing capabilities, sometimes a very soft elastomer is sandwiched between two or more elastomers which are more rigid than the soft elastomer. The rigid elastomers create the axial resistance needed to maintain reasonable compressive forces in the soft elastomer during tube penetration and following withdrawal.

There are two major drawbacks of the above described plug type septa. First, the septum must have sufficient axial depth to maintain compression in the center of the plug during tube penetration and withdrawal. This makes space-critical applications difficult. Second, coring may occur during septum penetration. That is, during axial penetration the septum elastomer resists with an opposing axial reaction force causing a "cookie cutter" effect at the interface between the end of the tube wall and the septum elastomer. This can cut a small core from the material, possibly plugging the tube.

It would be desirable then to provide a septum which could be relatively thin, resists coring, and is simple to fabricate.

SUMMARY OF THE INVENTION

The present invention then, provides septum penetrable by a member and which maintains a seal following member penetration in an axial direction and withdrawal. The septum includes a first layer of resilient material having first and second opposed surfaces. A second layer extends across the first surface of the first layer and is in radial tension. The septum may also include a third layer which extends across the second surface of the first layer, which third layer is in radial tension.

The second and third layers are continuous and may be under any suitable radial tension, for example between 5 and 1000 newton/m, and optionally between 10 to 100 newton/m, or between 20 to 80 newton/m, A resilient material, such as a suitable polymer, may be used for any of the first, second, and third layers. Each of the layers may have any suitable thickness which will allow axial penetration of the member while maintaining a seal following penetration and member withdrawal. For example, each layer may have a thickness of less than 10 mm or 1 mm, such as between 0.01 to 10 mm, 0.02 mm to 2 mm, or 0.05 mm to 1 mm. The first layer may be held in compression by the second and third layers, with a force for example of between 5 and 1000 newton/m, and optionally between 10 to 100 newton/m, or between 20 to 80 newton/m. The foregoing tension and compression forces are radial forces as measured at the edge of the layers.

The present invention also provides a septum assembly which includes any rigid periphery which defines an opening, for example an opening into any chamber such as that of a vessel or conduit. The opening may support a septum of any type of the present invention. Optionally, the septum may be fastened to the periphery of such an opening. The opening in such an assembly may, for example, have an area of between 0.001 cm$^2$ to 100 cm$^2$, or 0.01 cm$^2$ to 50 cm$^2$, or even 2 cm$^2$ to 30 cm$^2$ or to 20 cm$^2$.

The present invention further provides a method of fabricating a septum such as a septum of the present invention. Such a method may include applying radial tension to the second layer (and third layer, when present) and bonding the second layer to the first layer of resilient material such that the bonded second layer (and third layer, when present) is under tension. The tension can be applied either prior to or after bonding. For example, the tension may be applied prior to and during bonding to the first layer. One way for providing tension in this situation is by pulling on the layers. Alternatively, the tension may be applied after the bonding of the layers. For example, by means of chemical or thermal shrinkage.

Different embodiments of septa and methods and devices of the present invention can provide any or more of a number of useful features. For example, the septa may be made thin while still maintaining the sealing following axial tube penetration and withdrawal. Further, septa of the present invention can resist coring, be simple to fabricate, and require only a low force for member penetration.

BRIEF DESCRIPTION OF THE DRAWINGS

Embodiments of the invention will now be described with reference to the drawings, in which:

FIG. 1 illustrates a conventional prior art septum used to close a vessel, as described above;

FIG. 2 is a cross-section of a septum of the present invention;

To facilitate understanding, identical reference numerals have been used, where practical, to designate identical elements that are common to the figures.

DETAILED DESCRIPTION OF EMBODIMENTS OF THE INVENTION

Figure 3:
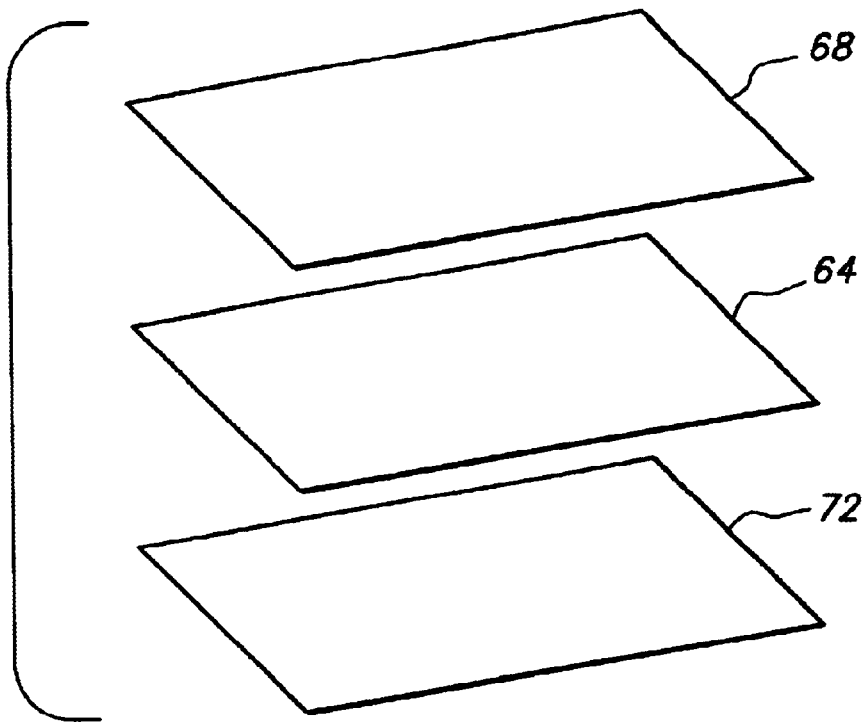
FIGS. 3 and 4 illustrates fabrication of a septum of the present invention using a method of the present invention.

In the present application, unless a contrary intention appears, words such as "front", "rear", "back", "top", "upper", and "lower", are all used in a relative sense only. Reference to a singular item (such as "an item"), includes the possibility that there may be plural of the same items present. It will be appreciated that while the axial and radial directions described herein are typically perpendicular to one another, they need not be and could, for example, be separated by less than ninety degrees (such as less than 45, less than 20 or less than 10 degrees). When reference is made to "shrinking" an outer layer or the like, or "expanding" an inner layer, this does not mean that under the conditions of restraint (particularly bonding to the other layer or layers) an actual change in physical dimensions must take place. Instead it is sufficient if shrinking or expansion of the layer would have occurred if that layer had not been otherwise restrained (by the other layers), such that tension or compression will be induced. All patents and other cited references are incorporated into this application by reference.

Referring first to FIG. 2, a septum 60 of the present invention includes a first layer 64 (sometimes referenced as the "inner layer") with a second layer 68 and a third layer 72 (either of which are sometimes referenced as the "outer layer") bound to first layer 64 and extending across first and second surfaces, respectively of first layer 64. Each of the layers is of a continuous sheet construction. Outer layers 68, 72 are held in radial tension (as indicated by arrows 46 in FIG. 2), while inner layer 64 is held in compression (with a force acting at least in the direction of arrows 40, 42) by outer layers 68, 72. Any of the layers 64, 68, 72 can be made of a resilient polymer such as natural and synthetic rubbers, for example butadiene polymers and copolymers, neoprene, chloroprene and the like. Typically though, outer layers 68, 72 will be of a less resilient (that is, less elastic) material than inner layer 64. The material should of course be selected to be compatible with any chemicals to which septum 60 may be exposed in the intended use. Each of layers 64, 68, 72 may have a thickness, for example, of less than 1 mm or even 0.1 mm or less. For example, the layer thicknesses may be such that the total septum 60 thickness is less than 2 mm, or even less than 1 mm or 0.2 mm. As to the tension in each outer layer 68, 72, and compression in inner layer 64, this may be any of the values already discussed above.

Figure 4:
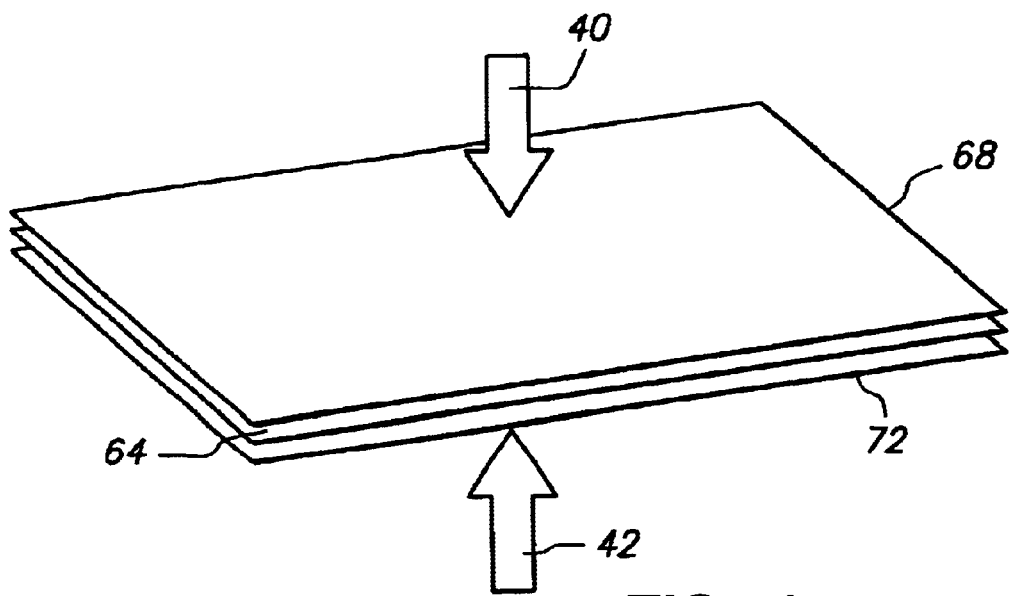

Septum 60 may be fabricated in any of a number of ways. One such way is illustrated in FIGS. 3 and 4. In this method outer layers 68, 72 may be made of a heat shrink film such as a heat shrinkable polyester film, perfluorinated hydrocarbon polymers (such as TEFLON), or other suitable crosslinkable polymer, while inner layer 64 is a thin membrane of an elastomer (see particularly FIG. 3). The three layers may then be bonded together with a flexible adhesive or other suitable means (such as, less desirably, stitching). The resulting composite laminate can then be heat treated to shrink the outer layers. This results in the outer layers 68, 72 being held under tension while the tensioned outer layers hold inner layer 64 under compression. Clamping the laminate between platens and exerting pressure in opposite axial directions 40, 42, while cooling, assures flatness (see particularly HG. 4).

Figure 5:
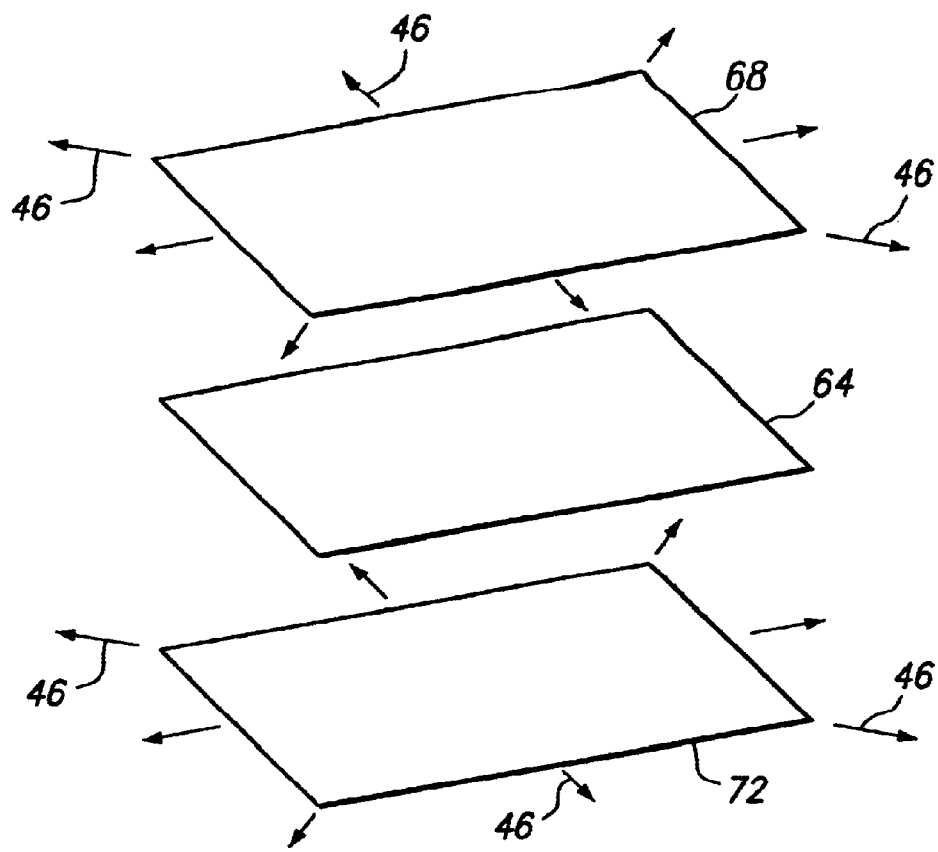
FIG. 5 illustrates an alternate method of the present invention.

Another method of fabricating septum 60 is illustrated in FIG. 5. In this method a layer of elastomeric material is used for each of the outer layers 68, 72 and inner layer 64. The outer layers 68, 72 are pulled and stretched and held under the resulting tension while they are bonded to opposite surfaces of inner layer 64 which is in its relaxed state. Once bonded, the outer layers 68, 72 are released. The resulting laminate will then reach an equilibrium with outer layers 68, 72 in tension and inner layer 64 in compression. Additionally, each of the outer layers 68, 72 could be of less elastic film than inner layer 64 and could be further laminated on their outside to additional elastic layers (such as a polyester film which is not of the heat-shrinkable type, not shown) to increase stiffness of septum 60 and reduce stretching of outer layers 68, 72 during puncture by a member.

Other ways could be used to create septum 60, where the inner layer 64 is maintained in compression while the outer layers 68, 72 maintain this compression due to radial tension. Such other methods may include, for example, making one or more of outer layers 68, 72 of a suitable material and treating them chemically, after binding to inner layer 64, to cause them to shrink (thereby inducing the radial tension). Alternatively, thermal means could be used such as by pre-chilling inner layer 64 to shrink prior to bonding to outer layers 68, 72. The outer layers 68, 72 could also be heated to expand them after bonding. The inner layer 64 can be placed under compression after bonding by chemical means, such as by absorption of liquid when the inner layer 64 is made of an appropriate liquid absorbing.polymer which expands when wetted. Similarly, outer layers 68, 72 can be induced to shrink chemically such as by application of a suitable solvent where the outer layers are formulated to shrink during solvent evaporation.

Figure 6:
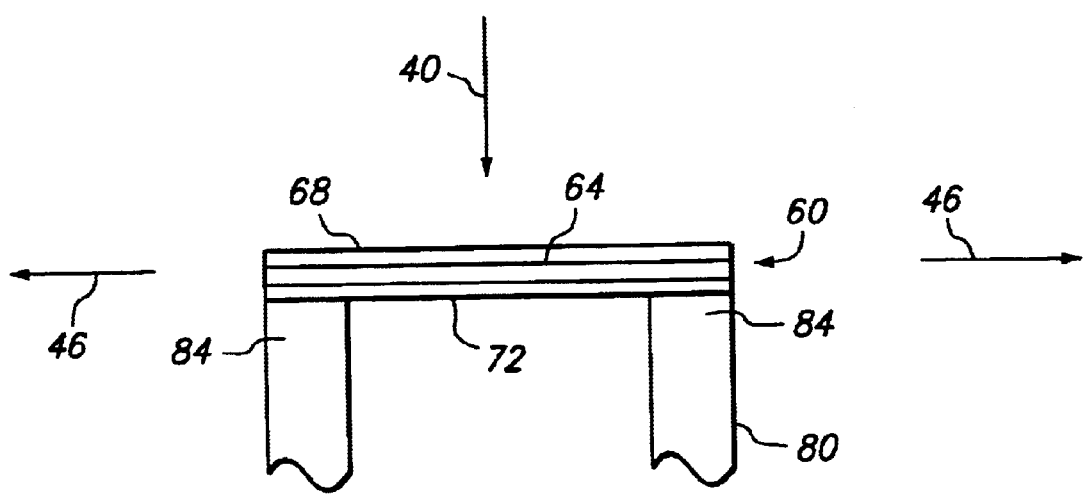
FIG. 6 illustrates a septum assembly of the present invention.

The septum 60 may be used, for example, by supporting or attaching it to extend across a rigid periphery defining an opening, such as an upper circular end 84 of a vessel 80 (as illustrated in FIG. 6). The opening may have any suitable area, such as 01. to 100 cm$^2$ or 2 to 50 cm$^2$. A hollow member in the form of needle 30 may penetrate septum 60 in axial direction 40 to provide or remove contents to vessel 80. Septum 60 maintains a seal around the puncturing member, and re-closes to maintain the seal in vessel 80 when the member is withdrawn from septum 60. Membrane 60 offers little reaction force in the axial direction during member penetration, and thus the penetrating tube tends to split the layers of membrane 60 open rather then cut a core from it. When the tube is removed, the compressed elastomer of inner layer 64 in particular forces the hole closed to maintain the seal in vessel 80.

Figure 7:
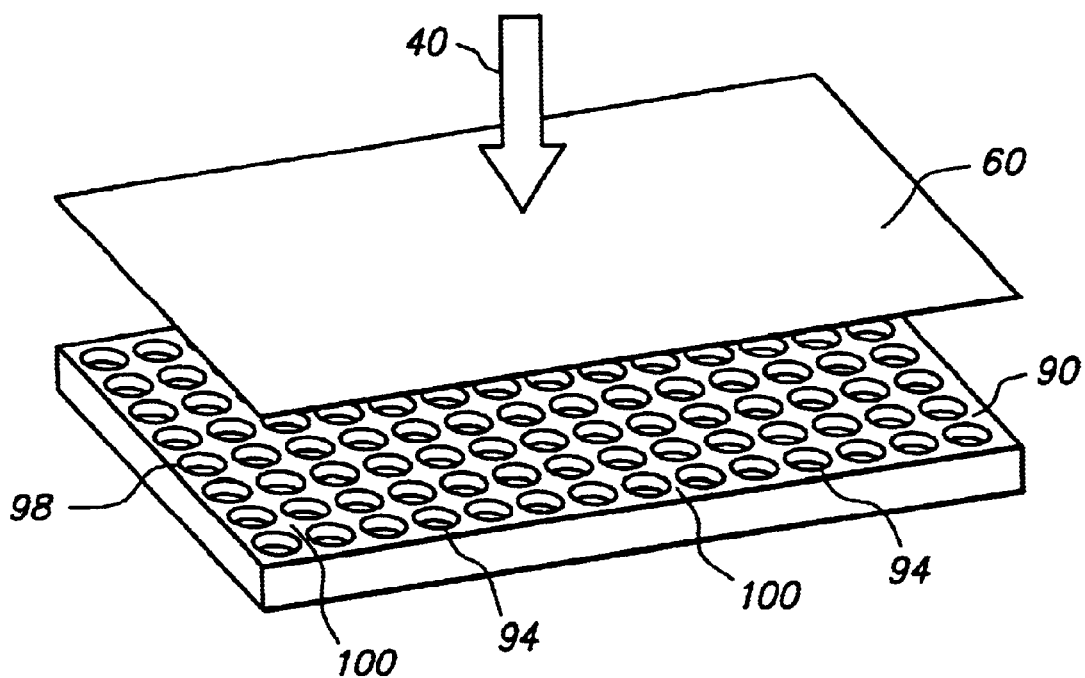
FIG. 7 is a perspective view showing assembly of a septum and multiple vessels to create multiple septa assemblies of the present invention.

In addition to being used to close a single opening of a vessel, a septum of the present invention can be used to close multiple vessels in a manner such as illustrated in FIG. 7. In FIG. 7, a single septum 60 is used to close multiple wells 94 opening to a top surface of a multi-well plate 90. Septum 60 in this case is sealed to a top surface 98 of a multi-well plate 90, typically by sealing at all areas 100 on top surface 98 between wells 94, so as to close each well 94. Alternatively, septum 60 may be sealed only around the periphery of top surface 98. Unlike simple plate or foil closures, septum 60 can be repeatedly pierced multiple times by a needle while still maintaining sealing of wells 94, thereby reducing the threat of contamination and simplifying handling. Further, in this or any application, by using transparent materials for each of the layers of the septum, visual inspection of the well (or other vessel) contents is possible.

A septum of the present invention may offer one or more advantages over conventional septa such as that of FIG. 1. For example, such septa can be manufactured in a high speed web process. Such septa can also be bonded or otherwise sealed on a surface of a vessel or vessel assembly without insertion into an opening. For typical applications, only a small amount of materials is required for fabrication of a septum of the present invention. Since septa of the present invention can be made thin, only a small amount of space is required in typical applications and the force required for piercing can be low. Additionally, the dynamics of piercing a septum of the present invention provides little in the way of the reaction forces necessary to produce coring.

Various further modifications to the particular embodiments described above are, of course, possible. Accordingly, the present invention is not limited to the particular embodiments described in detail above.

What is claimed is:

1. A septum penetrable by a member and which maintains a seal following member penetration in an axial direction and withdrawal, comprising:
   a first layer of resilient material having first and second opposed surfaces; and
   a second continuous layer extending across, and bonded to, the first surface of the first layer and which is in radial tension to hold the first layer in radial compression.

2. A septum according to claim 1 additionally comprising a third layer extending across the second surface of the first layer, which third layer is in radial tension.

3. A septum according to claim 2 wherein the third layer is continuous.

4. A septum according to claim 2 wherein each of the second and third layers are under a tension of between $10^2$ to $10^6$ newton/m$^2$.

5. A septum according to claim 2 wherein each of the second and third layers comprise a resilient material.

6. A septum according to claim 5 wherein each of the first, second and third layers comprise a resilient polymer.

7. A septum according to claim 5 wherein each of the first, second and third layers has a thickness of less 10 mm.

8. A septum according to claim 2 wherein the first layer is held in compression by the second and third layers.

9. A septum according to claim 8 wherein the first layer is held in a compression of between 5 to 1000 newton/m.

10. A septum assembly comprising a chamber having a rigid periphery defining an opening into the chamber, and a septum of claim 1 extended across, and supported by, the periphery.

11. A septum assembly comprising a chamber having a rigid periphery defining an opening into the chamber, and a septum assembly of claim 2 extended across, and supported by, the periphery.

12. A septum assembly of claim 11 wherein the opening has an area of 0.001 to 100 cm$^2$.

13. A septum assembly of claim 11 wherein the opening has an area of 0.01 cm$^2$ to 50 cm$^2$.

* * * * *